US008766023B2

(12) United States Patent
Coggan

(10) Patent No.: US 8,766,023 B2
(45) Date of Patent: Jul. 1, 2014

(54) SYNTHESIS PROCESS

(75) Inventor: Jennifer A. Coggan, Cambridge (CA)

(73) Assignee: LG Display Co., Ltd., Seoul (KR)

( * ) Notice: Subject to any disclaimer, the term of this patent is extended or adjusted under 35 U.S.C. 154(b) by 1252 days.

(21) Appl. No.: 11/184,776

(22) Filed: Jul. 20, 2005

(65) Prior Publication Data
US 2007/0020481 A1    Jan. 25, 2007

(51) Int. Cl.
*C07C 1/00* (2006.01)
*C07C 7/00* (2006.01)

(52) U.S. Cl.
USPC .............. 585/26; 585/425; 585/427; 585/469

(58) Field of Classification Search
USPC ................................... 585/26, 469
See application file for complete search history.

(56) References Cited

U.S. PATENT DOCUMENTS

| | | | |
|---|---|---|---|
| 2,842,563 A * | 7/1958 | Hinegardner et al. ........ 552/265 |
| 3,172,862 A | 3/1965 | Gurnee et al. |
| 3,464,979 A * | 9/1969 | Barton ............................. 540/73 |
| 3,911,038 A * | 10/1975 | Maulding ....................... 585/312 |
| 4,020,109 A * | 4/1977 | Fleck et al. .................... 568/421 |
| 4,356,429 A | 10/1982 | Tang |
| 4,539,507 A | 9/1985 | Van Slyke et al. |
| 4,885,211 A | 12/1989 | Tang et al. |
| 5,150,006 A | 9/1992 | Van Slyke et al. |
| 5,151,629 A | 9/1992 | Van Slyke |
| 5,429,884 A | 7/1995 | Namiki et al. |
| 5,516,577 A | 5/1996 | Matsuura et al. |
| 5,846,666 A | 12/1998 | Hu et al. |
| 5,935,721 A | 8/1999 | Shi et al. |
| 6,048,630 A | 4/2000 | Burrows et al. |
| 6,268,072 B1 | 7/2001 | Zheng et al. |
| 6,361,886 B2 | 3/2002 | Shi et al. |
| 6,465,115 B2 | 10/2002 | Shi et al. |
| 6,613,457 B2 | 9/2003 | Zheng et al. |
| 6,740,263 B2 * | 5/2004 | Park et al. ...................... 252/700 |
| 2003/0082401 A1 | 5/2003 | Zheng et al. |
| 2003/0165715 A1* | 9/2003 | Yoon et al. .................... 428/690 |
| 2004/0018380 A1 | 1/2004 | Aziz et al. |
| 2004/0126617 A1 | 7/2004 | Brown et al. |
| 2005/0104511 A1* | 5/2005 | Liao et al. ...................... 313/504 |
| 2005/0127831 A1 | 6/2005 | Takeuchi et al. |
| 2005/0211958 A1* | 9/2005 | Conley et al. .................. 252/583 |
| 2005/0245752 A1 | 11/2005 | Conley et al. |
| 2005/0260450 A1* | 11/2005 | Yamagata et al. ............ 428/690 |

FOREIGN PATENT DOCUMENTS

| | | |
|---|---|---|
| CN | 1583691 A | 2/2005 |
| EP | 1 289 029 A2 | 3/2003 |
| EP | 1 333 018 A1 * | 8/2003 |
| EP | 1 435 669 A2 | 7/2004 |
| EP | 1 500 922 A2 | 1/2005 |
| EP | 1 553 154 A1 | 7/2005 |
| EP | 1 555 855 A2 | 7/2005 |
| WO | WO 2005/110950 A1 | 11/2005 |

OTHER PUBLICATIONS

Duveen et al., "The Photo=oxides of 9:10-Dixenylanthracene and 9:10-Diphenyl-2-methylanthracene," Journal of the Chemical Society, pp. 116-118, 1939.*
Kan et al., "Highly-efficient blue electroluminescence based on two emitter isomers," Applied Physics Letters, vol. 84, No. 9, pp. 1513-1515, Mar. 2004.*
Kauffman et al., "Improved Apparatus for Continuous column Chromatography," Journal of Chemical Education, vol. 53, No. 1, pp. 33, Jan. 1976.*
Kotha et al., "Synthesis of Symmetrical and Unsymmetrical 9,10-Diarylanthracene Derivatives via Bis-Suzuki-Miyaura Cross-Coupling Reaction," Synthesis, No. 4, pp. 549-557, Feb. 19, 2004.*
Rimmer et al., "The Reduction of Some 9,10-Dihydroxy-9,10-dihydro Derivatives of Phenanthrene and Anthracene", J. Am. Chem. Soc. 72(5), 1950, pp. 2298-2299.*
Yang et al., Two-Photon Absorption Properties of 2,6-Bis-(styryl)anthracene Derivatives: Effects of Donor-Acceptor Substituents and the π Center, Chemistry-A European Journal, 2005, vol. II (14), pp. 4191-4198.
Balaganesan, B. et al.; "Synthesis of t-Butylated Diphenylanthracene Derivatives as Blue Host Materials for OLED Applications"; Tetrahedron Letters 2003, 44, 5747-5750.
Yang, W. J. et al.; "2, 6-Bis(styryl)Anthracene Derivatives with Large Two-Photon Cross-Sections"; Chem. Commun.; 2618-1619, (2003).
Kotha, S. et al.; "Synthesis of 9,10-Diarylanthracene Derivatives via bis Suzuki-Miyaura Cross-Coupling Reaction"; Synlett 2002, No. 3 04032002, 451-452.
Jones, S. et al.; "An Improved Procedure for the Preparation of 9,10-Dibromoanthracene"; Synthetic Communications 2001, 31(12); 1799-1802.

* cited by examiner

*Primary Examiner* — Marie R. Yamnitzky
(74) *Attorney, Agent, or Firm* — McKenna Long & Aldridge LLP

(57) ABSTRACT

A process for preparing a substituted or unsubstituted 9,10-diarylanthracene including reacting an organometallic substituted or unsubstituted aryl compound with a substituted or unsubstituted anthraquinone to yield a substituted or unsubstituted diol; and reacting the substituted or unsubstituted diol with a reducing agent to yield the substituted or unsubstituted 9,10-diarylanthracene is disclosed. An electroluminescent device comprising a light-emitting layer comprising the substituted or unsubstituted 9,10-diarylanthracene is also disclosed.

5 Claims, 3 Drawing Sheets

SYNTHESIS PROCESS

FIELD OF THE DISCLOSURE

The present disclosure relates to a process for preparing a substituted or unsubstituted 9,10-diarylanthracene.

BACKGROUND OF THE DISCLOSURE

Organic light emitting devices (OLEDs) are useful for display applications and in particular, mobile hand held display applications. To achieve efficient electroluminescence OLEDs have typically been manufactured to include separate layers of a hole transport material (HTM) and an emitting electron transport material (ETM). During operation, an applied electric-field causes positive charges (holes) and negative charges (electrons) to be respectively injected from the anode and the cathode of the OLED to recombine and thus produce light emission. In other known OLED displays, the hole transport and electron transport layers are doped with organic dyes in order to enhance the efficiency or to improve the stability of the OLED. OLEDs have also been developed in which hole transport material and emitting electron transport material are mixed together in one single layer.

One problem associated with OLEDs is the development of high-performance materials with desirable properties. Many new materials with RGB (red, green, blue) emitting colors have been developed to meet the requirements for full-color displays. While green emitting materials are relatively well developed for OLEDs, satisfactory blue materials with good color purity, high efficiency, and good stability are still in demand. One such known material is 2-tert-butyl-9,10-bis-(β-naphthyl)anthracene.

In a typical OLED, the light emitting layer can be present between a hole transport layer and an electron transport layer. The light-emitting can comprise a host material doped with a guest material (dopant), as shown in FIG. 1. The light emitting layer can provide an efficient site for the recombination of the injected hole-electron pair followed by energy transfer to the guest material which can produce highly efficient electroluminescence. Ideally, the same host material should be able to be doped with an appropriate guest material to be able to produce red, green, or blue emission depending on the color emission from the guest material. It can be difficult to find a larger energy gap host material than the blue emitting guest material. The compound 2-tert-butyl-9,10-bis-(β-naphthyl)anthracene (TBADN) can have an excellent wide energy gap host for color OLEDs.

SUMMARY OF THE DISCLOSURE

In various aspects of the disclosure, there is provided a process for preparing a substituted or unsubstituted 9,10-diarylanthracene comprising reacting an organometallic substituted or unsubstituted aryl compound with a substituted or unsubstituted anthraquinone to yield a substituted or unsubstituted diol; and reacting the substituted or unsubstituted diol with a reducing agent to yield the substituted or unsubstituted 9,10-diarylanthracene; a process for preparing a substituted or unsubstituted 9,10-diarylanthracene comprising reacting a substituted or unsubstituted diol with a reducing agent to yield the substituted or unsubstituted 9,10-diarylanthracene; and an electroluminescent device comprising a light-emitting layer comprising a substituted or unsubstituted 9,10-diarylanthracene prepared by reacting an organometallic substituted or unsubstituted aryl compound with a substituted or unsubstituted anthraquinone to yield a substituted or unsubstituted diol; and reacting the substituted or unsubstituted diol with a reducing agent to yield the substituted or unsubstituted 9,10-diarylanthracene.

Additional objects and advantages of the disclosure will be set forth in part in the description which follows, and in part will be obvious from the description, or may be learned by practice of the disclosure. The objects and advantages of the disclosure will be realized and attained by means of the elements and combinations particularly pointed out in the appended claims.

It is to be understood that both the foregoing general description and the following detailed description are exemplary and explanatory only and are not restrictive of the disclosure, as claimed.

The accompanying drawings, which are incorporated in and constitute a part of this specification, illustrate one (several) embodiment(s) of the disclosure and together with the description, serve to explain the principles of the disclosure.

DESCRIPTION OF THE DISCLOSURE

Figure 1:
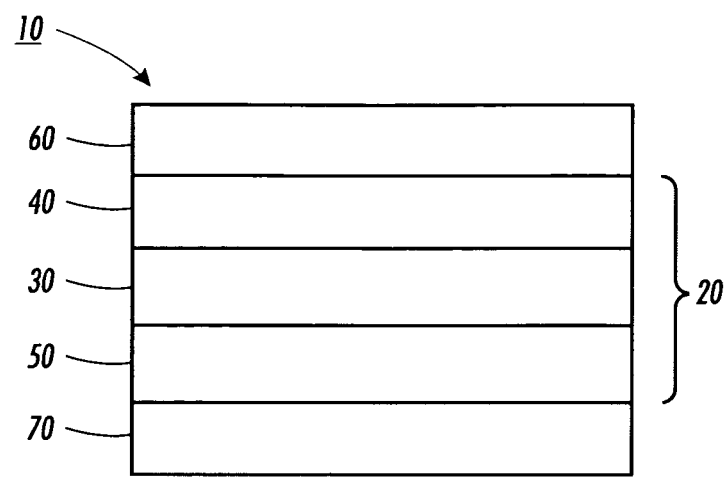
FIG. 1 illustrates a schematic of an OLED according to one embodiment of the present disclosure, having an electron injection and transporting zone, a mixed charge transport layer and a hole injection and transporting region.

Reference will now be made in detail to the present embodiments of the disclosure, examples of which are illustrated in the accompanying drawings. Wherever possible, the same reference numbers will be used throughout the drawings to refer to the same or like parts.

The present disclosure relates to a process for preparing a substituted or unsubstituted 9,10-diarylanthracene comprising reacting an organometallic substituted or unsubstituted aryl compound with a substituted or unsubstituted anthraquinone to yield a substituted or unsubstituted diol; and reacting the substituted or unsubstituted diol with a reducing agent to yield the substituted or unsubstituted 9,10-diarylanthracene.

The substituted or unsubstituted 9,10-diarylanthracene can be represented by formula (1):

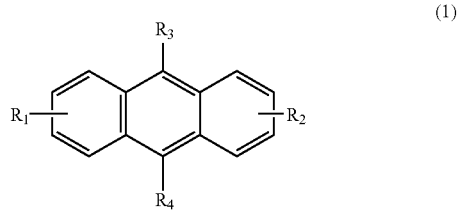

wherein $R_1$ and $R_2$ can be individual substituents or a group of substituents, each substituent can be individually selected from the following groups: Group 1—hydrogen, or alkyl of from about 1 to about 24 carbon atoms; Group 2—aryl or substituted aryl of from about 5 to about 20 carbon atoms; Group 3—carbon atoms from about 4 to about 24, wherein the carbon atoms can complete a fused aromatic ring of anthracenyl; pyrenyl, or perylenyl; Group 4—heteroaryl or substituted heteroaryl of from about 5 to about 24 carbon atoms, wherein the carbon atoms can complete a fused heteroaromatic ring of furyl, thienyl, pyridyl, quinolinyl and other heterocyclic systems; Group 5—alkoxyl, amino, alkyl amino, or aryl amino of from about 1 to about 24 carbon atoms; and Group 6—halogen atoms, such as fluorine, chlorine, bromine or cyano; and wherein $R_3$ and $R_4$, which can be the same or different, can be individually selected from the group consisting of groups 2, 3, 4 and the aryl amino of 5 as defined above. In an embodiment, the substituted or unsubstituted 9,10-diarylanthracene can be 2-tert-butyl-9,10-bis-(β-naphthyl)anthracene (TBADN).

In an embodiment, the process can be illustrated by the following reaction scheme:

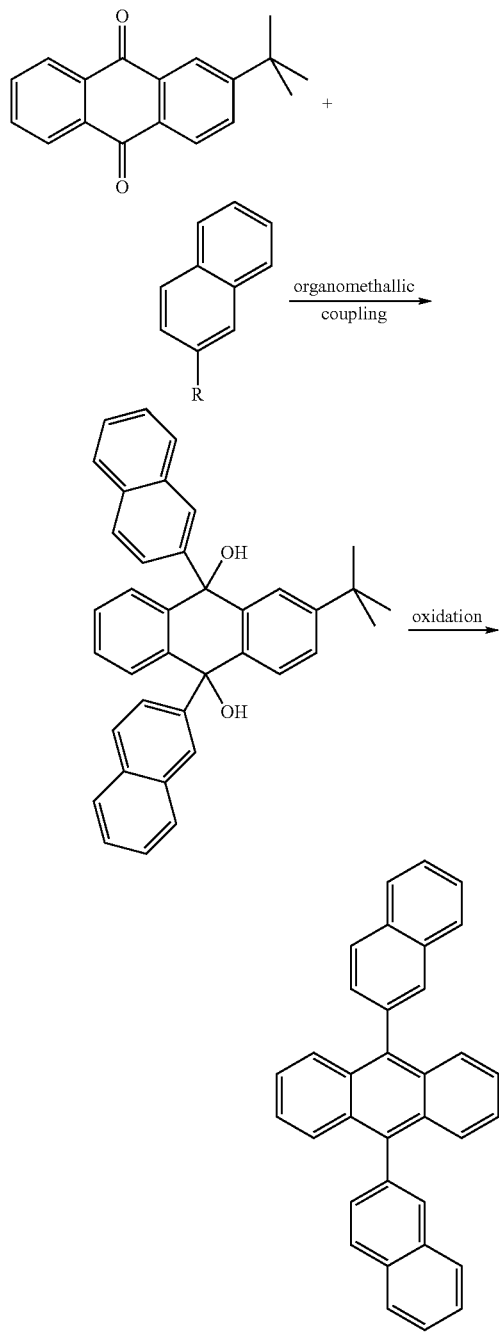

The anthraquinone can be substituted with typical substituents including alkyl groups, alkylene groups, aryl groups, arylene groups, alkoxy groups, aryl groups, aryloxy groups, and halogens, such as fluoride, chloride, and bromide. The various alkyl and alkylene moieties can comprise from about 1 to about 8 carbon atoms, such as, for example, from about 2 to about 7 carbon atoms, and as a further example about 4 carbon atoms. The cycloalkyl moieties can comprise from about 3 to about 10 carbon atoms, for example from about 5 to about 7 carbon atoms, and as a further example from about 5 to about 6 carbon atoms. The aryl and arylene moieties can be phenyl and phenylene moieties. In an embodiment, the anthraquinone can be substituted with a t-butyl group. For example, the substituted or unsubstituted anthraquinone can be 2-(t-butyl)anthraquinone.

The substituted or unsubstituted anthraquinone can be subjected to an organometallic coupling reaction with an organometallic substituted or unsubstituted aryl compound. The organometallic substituted or unsubstituted aryl compound can be prepared from a halogenated substituted or unsubstituted aryl group. The organometallic substituted aryl compound and the halogenated substituted aryl compound can each be individually substituted with typical substituents including alkyl groups, alkylene groups, aryl groups, arylene groups, alkoxy groups, aryl groups, aryloxy groups, and halogens, such as fluoride, chloride, and bromide. The various alkyl and alkylene moieties can comprise from about 1 to about 8 carbon atoms, such as, for example, from about 2 to about 7 carbon atoms, and as a further example about 4 carbon atoms. The cycloalkyl moieties can comprise from about 3 to about 10 carbon atoms, for example from about 5 to about 7 carbon atoms, and as a further example from about 5 to about 6 carbon atoms. The aryl and arylene moieties can be phenyl and phenylene moieties.

In an embodiment, the halogenated substituted or unsubstituted aryl compound can be a compound represented by formula (2):

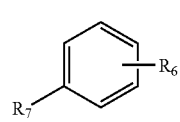

(2)

wherein $R_7$ can be a halogen, such as chloride, bromide or iodide and $R_6$ can be any of the substituents described for formula (1). In an embodiment, the halogenated substituted or unsubstituted aryl compound can be 2-bromonaphthalene.

The organometallic substituted or unsubstituted aryl compound can be prepared by reaction of the halogenated substituted or unsubstituted aryl compound as shown by formula (2) with a metal or organometallates. The metal can be chosen from magnesium, lithium, sodium, beryllium, calcium, zinc, copper, titanium, zirconium, manganese, palladium, and the like or can be chosen from organometallates such as (n-butyl)lithium and (t-butyl)lithium. The metal source can be metallocenes with ferrocene as an example. The term "metal" is understood to include all elements, such as silicon, arsenic, or boron, which are not metallic but are considered to be metalloids.

In an embodiment, the organometallic substituted or unsubstituted aryl compound can be prepared by addition of a metal or an organometallate such as n-butyllithium to the halogenated substituted or unsubstituted aryl compound over a period from about 1 minute to about one hour, for example from about 10 minutes to about 45 minutes, and as a further example about 15 minutes. The reaction can proceed from about 1 hour to about 5 hours, for example from about 2 hours to about 4 hours, and as a further example about 3 hours while the temperature can reach about room temperature (23° C.). The reaction temperature can be reduced to less than about room temperature, for example to less than about 0C., and as a further example to less than about −76° C. The substituted or unsubstituted anthraquinone can be added to the reaction. The reaction temperature can increase to greater than about −76° C., for example to greater than about 0C., and as a further example to about room temperature to yield a substituted or unsubstituted diol.

In an embodiment, the diol can be substituted with any of the typical substitutents of formula (1), such as an alkyl group, for example a t-butyl group. For example, the diol can be represented by formula (3):

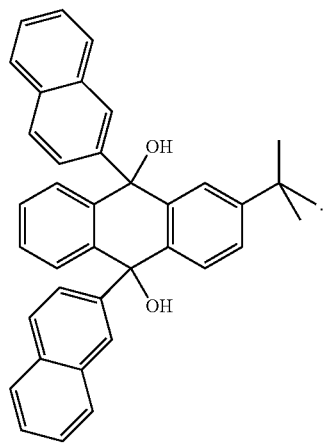

(3)

The substituted or unsubstituted diol can react with a reducing agent to yield the substituted or unsubstituted 9,10-diarylanthracene. The reducing agent can be chosen from stannous chloride, vanadous chloride, and titanous chloride in an acid such as acetic acid or hydrochloric acid and with or without water and can be conducted in a solvent such as dioxane. In an embodiment, the reducing agent can be potassium iodide in an acid such as acetic acid or hydrochloric acid and with or without potassium hypophosphite and optionally a solvent could be present. One of ordinary skill in the art would understand that other reagents including combinations of reagents can be used to affect this transformation.

The reducing agent can be added and the reaction temperature can be increased to at least about room temperature, for example to at least about 40° C., and as a further example to at least about 50° C. for a period of at least about 1 hour, for example at least about 2 hours, and as a further example at least about 3 hours. The reaction can be cooled to about room temperature, filtered, and washed.

The substituted or unsubstituted 9,10-diarylanthracene can be dried, and purified, for example by Kaufman column and sublimation at 320° C.

Figure 2:
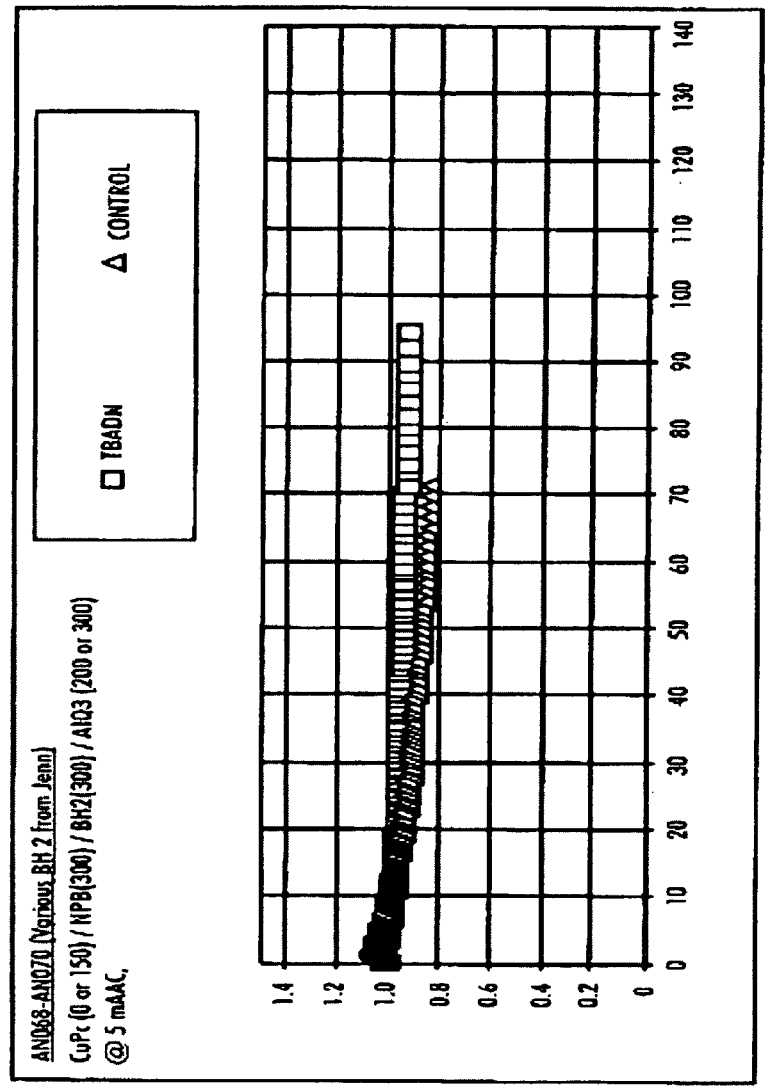
FIG. 2 illustrates the lifetime of the disclosed substituted or unsubstituted 9,10-diarylanthracene versus a commercially available TBADN over time.
Figure 3:
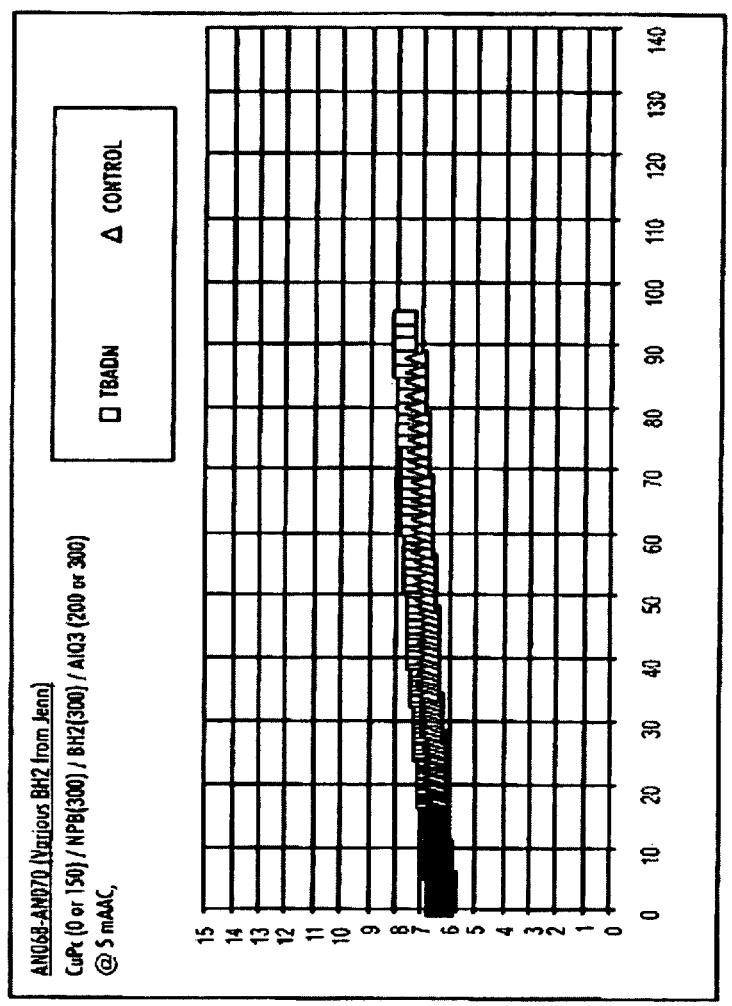
FIG. 3 illustrates the driving voltage versus time for the disclosed substituted or unsubstituted 9,10-diarylanthracene versus a commercially available TBADN.

As shown in FIG. 2, the substituted or unsubstituted 9,10-diarylanthracene can have an increased lifetime in an OLED compared to a commercially available TBADN. Moreover, as shown in FIG. 3, the substituted or unsubstituted 9,10-diarylanthracene can have about the same driving voltage versus time as compared to a commercially available TBADN.

An exemplary embodiment of an organic light emitting device (OLED) according to this disclosure is shown in FIG. 1. The organic light emitting device 10 can comprise a luminescent region 20 that comprises a mixed charge transport layer 30, an electron injection and transporting zone 40 and an optional hole injection and transporting zone 50. A cathode 60 can be provided adjacent and in contact with the electron injection and transporting zone 40. An anode 70 can be provided either directly adjacent and in contact with the mixed charged transport layer 30 or alternatively directly adjacent and in contact with the optional hole injection and transporting zone 50. While not illustrated in FIG. 1, the organic light emitting device can be provided on a substrate, with an anode 70 being directly adjacent and on top in contact with the substrate. An optional protective layer can be provided on top and in contact with the cathode 60. The anthracene compounds of the disclosure can be provided within the electron injection and transporting zone 40 and/or in the mixed charge transport layer 30.

In an embodiment, the electroluminescent (EL) device of the present disclosure can comprise a supporting substrate of, for example, glass, an anode thereover of, for example, indium tin oxide in a thickness of from about 1 to about 500 nanometers and for example from about 30 to about 100 nanometers (throughout the thickness ranges for each layer are examples and other suitable thickness may be selected), optionally a buffer layer in contact with the anode and comprised of a conductive component or hole transport materials in a thickness from about 5 to about 500 nanometers and for example from about 10 to about 100 nanometers, an organic hole injecting and transporting zone thereover of, for example, an aromatic tertiary amine in a thickness of from about 1 to about 200 nanometers and for example from about 5 to about 100 nanometers; an organic electron injection and transporting zone in contact with the hole injection and transporting zone comprised of the anthracene compounds of the formulas or encompassed by the formulas illustrated herein in a thickness of from about 5 to about 300 nanometers and for example from about 10 to about 100 nanometers, and in contact therewith a low work function metal as a cathode. In an embodiment, the hole injection and transporting zone or the electron injection and transporting zone can optionally further contain a luminescent material of, for example, from about 0.01 weight percent to about 10 weight percent of a fluorescent dye or from about 0.01 weight percent to about 25 weight percent of a phosphorescent dye.

In another embodiment, the EL device disclosed herein can comprise a supporting substrate of, for example, glass, an anode thereover of, for example, indium tin oxide in a thickness of from about 1 to about 500 nanometers and for example from about 30 to about 100 nanometers, optionally a buffer layer in contact with the anode and comprised of a conductive component or hole transport materials in a thickness from about 5 to about 500 nanometers and for example from about 10 to about 100 nanometers, an organic hole injection and transporting zone thereover of, for example, an aromatic tertiary amine in a thickness of from about 1 to about 200 nanometers and for example from about 5 to about 100 nanometers; a mixed charge transport layer comprised of an organic luminescent material of, for example, a fluorescent or a phosphorescent material, in a thickness of from about 1 to about 200 nanometers and for example from about 5 to about 100 nanometers, an organic electron injection and transporting zone in contact with the mixed charge transport layer comprised of the anthracene compounds of the formulas or encompassed by the formulas illustrated herein in a thickness of from about 5 to about 300 nanometers and for example from about 10 to about 100 nanometers, and in contact therewith a low work function metal as a cathode. In an EL device, light emission can originate from the mixed charge transport layer, which can optionally further comprise a luminescent dopant material of, for example, from about 0.01 weight percent to about 10 weight percent of a fluorescent dye or from about 0.01 weight percent to about 25 weight percent of a phosphorescent dye.

In yet another embodiment, the disclosed EL device can comprise a supporting substrate of, for example, glass, an anode thereover of, for example, indium tin oxide in a thickness of from about 1 to about 500 nanometers and for example from about 30 to about 100 nanometers, optionally a buffer layer in contact with the anode and comprised of a conductive component or hole transport materials in a thickness from about 5 to about 500 nanometers and for example from about 10 to about 100 nanometers, an organic hole injection and transporting zone thereover of, for example, an aromatic tertiary amine in a thickness of from about 1 to about 200 nanometers and for example from about 5 to about 100 nanometers; a mixed charge transport layer comprised of a hole transport material and an electron transport material in a thickness of from about 1 to about 200 nanometers and for example from about 5 to about 100 nanometers, an organic electron injection and transporting zone in contact with the mixed charge transport layer comprised of the anthracene compounds encompassed by the formulas illustrated herein in a thickness of from about 5 to about 300 nanometers and for example from about 10 to about 100 nanometers, and in contact therewith a low work function metal as a cathode. Typically, the mixed charge transport layer described herein can comprise from about 20 weight percent to about 80 weight percent of the hole transport material, and from about 80 weight percent to about 20 weight percent of the electron transport material, for example comprises, for example, from about 35 weight percent to about 65 weight percent of the hole transport material, and from about 65 weight percent to about 35 weight percent of the electron transport material. Suitable hole transport materials for forming the mixed layer include aromatic tertiary amines, indolocarbazoles, aromatic hydrocarbon compounds and mixtures thereof. The electron transport material of the mixed layer can comprise an anthracene compound encompassed by the formulas illustrated herein, or alternatively, the electron transport material can comprise known conventional electron transport materials such as metal chelates, stilbenes, triazines, aromatic hydrocarbons, and the like, and mixtures thereof. Furthermore, the mixed charge transport layer can further comprise a luminescent material of, for example, from about 0.01 weight percent to about 10 weight percent of a fluorescent luminescent material or from about 0.01 weight percent to about 25 weight percent of a phosphorescent luminescent material, or other luminescent materials where all weight percentages are based on the total weight of materials comprising the mixed layer. With respect to this embodiment, the organic electron injection and transporting zone, alternatively, can comprise known conventional electron transport materials such as metal chelates, stilbenes, triazines, aromatic hydrocarbons, and the like, and mixtures thereof. The electron transport material of the mixed charge transport layer can comprise anthracene compounds encompassed by the formulas illustrated herein. So long as at least one of the electron injection and transporting zone adjacent the cathode or the electron transport material present in the mixed charge transport layer (or both) comprises an anthracene compound of the disclosure. In this embodiment, it is also possible to provide an anthracene compound of the present disclosure both within the electron injection and transporting zone as well as in the mixed charge transport layer. Furthermore, where the mixed charge transporting layer contains hole transport material, a further hole injection and transporting zone can be optional within the luminescence region of the device.

It is understood by one of skill in the art that in each disclosed embodiment, the electron injection and transporting zone can comprise one or more layers where one or more of the layers can contain an anthracene compound. It is also understood that such layers can also incorporate one or more conventionally used electron transport materials such as for example $Alq_3$. Furthermore, the anthracene compounds can be incorporated in only a part or portion of any layer or layers of the electron injection and transporting zone.

All the organic layers described herein, the buffer layer, the hole transport layer, the light emitting layer, and the electron transport layer, can be formed by any suitable method, for example, by vacuum evaporation as is understood by one of skill in the art. The method can also be applied for forming any of the layers comprising more than one component. For example, the mixed layer can be formed by co-evaporating the hole transport material, the electron transport material, and the optional luminescent material.

The organic EL devices of the present disclosure can comprise a supporting substrate. Illustrative examples of supporting substrates include polymeric components, glass and the like, and polyesters like MYLAR®, polycarbonates, polyacrylates, polymethacrylates, polysulfones, quartz, and the like. Other substrates can also be selected provided, for example, it can effectively support the other layers, and that it does not interfere with the device functional performance. The thickness of the substrate can be, for example, from about 25 to about 1,000 microns or more, and, for example, from about 50 to about 500 microns depending, for example on the structural demands of the device.

Examples of the anode which is contiguous to the substrate, include positive charge injecting electrodes such as indium tin oxide, tin oxide, gold, platinum, or other suitable materials such as electrically conductive carbon, π-conjugated polymers such as polyaniline, polypyrrole, and the like with, for example, a work function equal to, or greater than about 4 electron volts, and more specifically, from about 4 to about 6 electron volts. The thickness of the anode can range from about 1 to about 500 nanometers with, for example, the range being dictated by the optical constants of the anode material. One non-limiting exemplary range of anode thickness can be from about 30 to about 100 nanometers.

An alternative buffer layer can be provided adjacent the anode of an electroluminescent device of the disclosure. The buffer layer primarily functions to facilitate efficient injection of holes from the anode, and improves the adhesion between the anode and the organic hole injection and transporting zone, thus further improving the device operation stability. The buffer layer can comprise conductive materials such as polyaniline and its acid-doped forms, polypyrrole, poly(phenylene vinylene), and known semiconductive organic materials; porphyrin derivatives disclosed in U.S. Pat. No. 4,356,429 (the disclosure of which is totally incorporated herein by reference), such as 1,10,15,20-tetraphenyl-21H,23H-porphyrin copper (II); copper phthalocyanine, copper tetramethyl phthalocyanine; zinc phthalocyanine; titanium oxide phthalocyanine; magnesium phthalocyanine; and the like.

Another class of hole transporting materials that can be selected for the buffer layer are the aromatic tertiary amines such as those disclosed in U.S. Pat. No. 4,539,507 (the disclosure of which is totally incorporated herein by reference). Representative examples of aromatic tertiary amines include, but are not limited to, bis(4-dimethylamino-2-methylphenyl) phenylmethane, N,N,N-tri(p-tolyl)amine, 1,1-bis(4-di-p- tolylaminophenyl)cyclohexane, 1,1-bis(4-di-p-tolylaminophenyl)-4-phenyl cyclohexane, N,N'-diphenyl-N,N'-bis(3-methylphenyl)-1,1'-biphenyl-4,4'-diamine, N,N'-diphenyl-N,N'-bis(3-methylphenyl)-1,1'-biphenyl-4,4'-diamine, N,N'-diphenyl-N,N'-bis(4-methoxyphenyl)-1,1'-biphenyl-4,4'-diamine, N,N,N',N'-tetra-p-tolyl-1,1'-biphenyl-4,4'-diamine, N,N'-di-1-naphthyl-N,N'-diphenyl-1,1'-biphenyl-4,4'-diamine, and the like. Another class of aromatic tertiary amines selected for the hole transporting layer is polynuclear aromatic amines, such as N,N-bis-[4'-(N-phenyl-N-m-tolylamino)-4-biphenylyl]aniline; N,N-bis-[4'-(N-phenyl-N-m-tolylamino)-4-biphenylyl]-m-toluidine; N,N-bis-[4'-(N-phenyl-N-m-tolylamino)-4-biphenylyl]-p-toluidine; N,N-bis-[4'-(N-phenyl-N-p-tolylamino)-4-biphenylyl]aniline; N,N-bis-[4'-(N-phenyl-N-p-tolylamino)-4-biphenylyl]-m-toluidine; N,N-bis-[4'-(N-phenyl-N-p-tolylamino)-4-biphenylyl]-p-toluidine; N,N-bis-[4'-(N-phenyl-N-p-chlorophenylamino)-4-biphenylyl]-m-toluidine; N,N-bis-[4'-(N-phenyl-N-m-chlorophenylamino)-4-biphenylyl]-m-toluidine; N,N-bis-[4'-(N-phenyl-N-m-chlorophenylamino)-4-biphenylyl]-p-toluidine; N,N-bis-[4'-(N-phenyl-N-m-tolylamino)-4-biphenylyl]-p-chloroaniline; N,N-bis-[4'-(N-phenyl-N-p-tolylamino)4-biphenylyl]-m-chloroaniline; N,N-bis-[4'-(N-phenyl-N-m-tolylamino)-4-biphenylyl]-1-aminonaphthalene and the like.

The buffer layer can also comprise aromatic tertiary amines and may further include a stabilizer as disclosed in U.S. Pat. No. 5,846,666 (the disclosure of which is totally incorporated herein by reference), a stabilizer comprising certain hydrocarbon compounds such as rubrene, 4,8-diphenylanthracene, and the like. The buffer layer can be prepared by forming one of the above compounds into thin film by known methods, such as vapor deposition or spin coating. The thickness of the buffer layer thus formed is not particularly limited, and can be in a range of from about 5 nanometers to about 300 nanometers, and for example from about 10 anometers to about 100 nanometers.

The hole injection and transporting zone can comprise a hole transporting material with a thickness ranging from about 1 nanometer to about 200 nanometers, and for example from about 5 nanometers to about 100 nanometers. Any conventional suitable aromatic amine hole transporting material described for the buffer layer can also be selected for forming this layer.

An exemplary class of hole transporting materials selected for forming the hole injection and transporting zone or for use as a hole transport material in the mixed charge transport layer are N,N,N',N'-tetraaryl benzidines, such as N,N'-diphenyl-N,N'-bis(4-methoxyphenyl)-1,1'-biphenyl-4,4'-diamine, N,N,N',N'-tetra-p-tolyl-1,1'-biphenyl-4-,4'-diamine, N,N'-di-1-naphthyl-N,N'-diphenyl-1,1'-biphenyl-4,4'-diamine, and the like, and 4,4'-bis(9-carbazolyl)-1,1'-biphenyl compounds, such as 4,4'-bis(9-carbazolyl)-1,1'-biphenyl compounds include 4,4'-bis(9-carbazolyl)-1,1'-biphenyl and 4,4'-bis(3-methyl-9-carbazolyl)-1,1'-biphenyl, and the like.

Non-limiting examples of luminescent materials suitable for use in the mixed charge transport layer include the metal chelates of 8-hydroxyquinoline as disclosed in U.S. Pat. Nos. 4,539,507; 5,151,629, and 5,150,006 (the disclosures of which are totally incorporated herein by reference). Illustrative specific examples of luminescent materials or compounds include tris(8-hydroxyquinolinate)aluminum, an example of one, tris(8-hydroxyquinolinate)gallium, bis(8-hydroxyquinolinate)magnesium, bis(8-hydroxyquinolinate)zinc, tris(5-methyl-8-hydroxyquinolinate)aluminum, tris(7-propyl-8-quinolinolato)aluminum, bis[benzo{f}-8-quinolinate]zinc-, bis(10-hydroxybenzo[h]quinolinate)beryllium, and the like. Also, another exemplary class of luminescent materials includes butadienes, such as 1,4-diphenylbutadiene and tetraphenylbutadiene, and stilbenes, and the like as illustrated in U.S. Pat. Nos. 4,356,429 and 5,516,577 (the disclosures of which are totally incorporated herein by reference).

The fluorescent materials can be present in, for example, from about 0.01 to about 10 weight percent, and for example from about 1 to about 5 weight percent of the layer. Illustrative examples of fluorescent materials include dyes selected, for example, from of coumarin, dicyanomethylene pyranes, polymethine, oxabenzanthrane, xanthene, pyrylium, carbostyl, perylene, and the like; a dye selected from quinacridone derivatives. Illustrative examples of quinacridone dyes include quinacridone, 2-methylquinacridone, 2,9-dimethylquinacridone, 2-chloroquinacridone, 2-fluoroquinacridone, 1,2-benzoquinacridone, N,N'-dimethylquinacridone, N,N'-dimethyl-2-methylquinacridone, N,N'-dimethyl-2,9-dimethylquinacridone, N,N'-dimethyl-2-chloroquinacridone, N,N'-dimethyl-2-fluoroquinacridone, N,N'-dimethyl-1,2-benzoquinacridone, and the like. An exemplary class of fluorescent materials are fused ring fluorescent dyes, examples of which are perylene, rubrene, anthracene, coronene, phenanthrecene, pyrene and the like, as illustrated in U.S. Pat. No. 3,172,862 (the disclosure of which is totally incorporated herein by reference). Also, fluorescent materials that can be used as a dopant include butadienes, such as 1,4-diphenylbutadiene and tetraphenylbutadiene, and stilbenes, and the like as illustrated in U.S. Pat. Nos. 4,356,429 and 5,516,577 (the disclosures of which are totally incorporated herein by reference).

The phosphorescent dye can be selected from, for example, organometallic compounds containing a heavy metal atom that can result in strong spin-orbit coupling, such as disclosed in Baldo et. al., "Highly efficient organic phosphorescent emission from organic electroluminescent devices", *Letters to Nature*, Volume 395, pp 151-154 (1998). Non-limiting examples include 2,3,7,8,12,13,17,18-octaethyl-21H,23H-phorpine platinum(II) (PtOEP) and others, such as, for example, those disclosed in U.S. Pat. No. 6,048,630 (the disclosure of which is totally incorporated herein by reference), and fac tris(2-phenylpyridine)iridium (Ir(ppy)$_3$).

The cathode can comprise any suitable material such as a metal, including high, for example from about 4.0 eV to about 6.0 eV, or low work function component, such as metals with, for example, an eV of from about 2.5 eV to about 4.0 eV (electron volts). The cathode can be derived from a combination of a low work function metal (about 4 eV, for example from about 2 to about 4 eV) and at least one other metal. Effective proportions of the low work function metal to the second or one other metal are from less than about 0.1 percent to about 99.9 percent by weight. Illustrative examples of low work function metals include alkaline metals such as lithium or sodium, Group 2A or alkaline earth metals such as beryllium, magnesium, calcium, or barium, and Group III metals including rare earth metals and the actinide group metals such as scandium, yttrium, lanthanum, cerium, europium, terbium, or actinium. Lithium, magnesium and calcium can be, for example, low work function metals.

The thickness of cathode can range from, for example, about 10 nanometers to about 500 nanometers. The Mg:Ag cathodes of U.S. Pat. No. 4,885,211 (the disclosure of which is totally incorporated herein by reference), constitute one exemplary cathode construction. Another exemplary cathode described in U.S. Pat. No. 5,429,884 (the disclosure of which are totally incorporated herein by reference), wherein the cathodes are formed from lithium alloys with other high work function metals such as aluminum and indium.

Both the anode and the cathode of the EL devices of the present disclosure can comprise a protective coating thereon as is understood by one of skill in the art. Furthermore, the anode and cathode can be of any convenient forms. A thin conductive layer can be coated onto a light transmissive substrate, for example a transparent or substantially transparent glass plate or plastic film. The EL device can include a light transmissive anode formed from tin oxide or indium tin oxide coated on a glass plate. Also, very thin, for example less than about 200 Angstroms, and more specifically, from about 75 to about 150 Angstroms, light-transparent metallic anodes can be used, such as gold, palladium, and the like. In addition, transparent or semitransparent thin layers, for example from 50 to about 175 Angstroms of conductive carbon or conjugated polymers such as polyaniline, polypyrrole, and the like can be selected as anodes. Any light transmissive polymeric film can be employed as the substrate. Additional suitable forms of the anode and cathode are illustrated in U.S. Pat. No. 4,885,211 (the disclosure of which is totally incorporated herein by reference).

An optional protective layer provided over and in contact with the cathode can comprise any suitable metal such as silver, gold, or non-conductive materials such as silicone oxide and the like.

EXAMPLE I

The 2-bromonaphthalene (11.75 g, 56.76 mmol) was placed into a 500 mL round bottom flask under argon which was dissolved into anhydrous THF (150 mL). The reaction was cooled to −78° C. (dry ice/acetone) and the "BuLi (28.4 mL, 56.76 mmol) was added slowly over 15 minutes. The reaction was stirred for 3 hours while the reaction warmed to room temperature. The reaction was cooled again to −78° C. and the 2-$^t$butylanthraquinone (5.0 g, 18.92 mmol) (dissolved in 20 mL THF) was added dropwise to the reaction. Once the addition was complete the reaction was allowed to stir at room temperature overnight. The reaction was quenched with saturated aqueous ammonium chloride solution and ethyl acetate (100 mL) was added. The aqueous layer was removed and the organic layer was washed twice more with ammonium chloride solution. The organic layer was collected, dried ($MgSO_4$) and conc in vacuo to give a yellow oil which was used directly in the next step. The product was dissolved into 1,4-dioxane (50 mL) and a mixture of 1:1 $H_2O$:AcOH (25 mL) was added. Tin(II) chloride dihydrate (21.34 g, 94.60 mmol) was added and the reaction was heated at 50° C. for 3 hours. The reaction was cooled to room temperature and methanol (50 mL) was added. The reaction mixture was filtered and the precipitate washed with methanol. The solid was collected, dried and was purified by Kaufmann column (alumina, cyclohexane). Further purification was achieved by sublimation (twice) at 320° C. to give >99% purity of TBADN.

EXAMPLE II

The bromobenzene (10 g, 63.69 mmol) was placed into a 500 mL round bottom flask under argon which was dissolved into anhydrous THF (150 mL). The reaction was cooled to −78° C. (dry ice/acetone) and the "BuLi (32 mL, 63.69 mmol) was added slowly over 15 minutes. The reaction was stirred for 3 hours while the reaction warmed to room temperature. The reaction was cooled again to −78° C. and the 2-t-butylanthraquinone (5.6 g, 21.23 mmol)(dissolved in 20 mL THF) was added dropwise to the reaction. Once the addition was complete the reaction was allowed to stir at room temperature overnight. The reaction was quenched with saturated aqueous ammonium chloride solution and ethyl acetate (100 mL) was added. The aqueous layer was removed and the organic layer was washed twice more with ammonium chloride solution. The organic layer was collected, dried ($MgSO_4$) and conc in vacuo to give a yellow oil which was used directly in the next step. The product was dissolved into 1,4-dioxane (50 mL) and a mixture of 1:1 $H_2O$:AcOH (75 mL) was added. Tin(II) chloride dihydrate (33.48 g, 148.73 mmol) was added and the reaction was heated at 50° C. for 3 hours. The reaction was cooled to room temperature and methanol (50 mL) was added. The reaction mixture was filtered and the precipitate washed with methanol. The solid was collected, dried and was purified by Kaufmann column (alumina, cyclohexane). Further purification was achieved by sublimation (twice) at 260° C. to give >99% purity of 2-tert-butyl-9,10-diphenylanthracene.

EXAMPLE III

The 2-bromotoluene (10 g, 58.47 mmol) was placed into a 500 mL round bottom flask under argon which was dissolved into anhydrous THF (150 mL). The reaction was cooled to −78° C. (dry ice/acetone) and the "BuLi (29.2 mL, 58.47 mmol) was added slowly over 15 minutes. The reaction was stirred for 3 hours while the reaction warmed to room temperature. The reaction was cooled again to −78° C. and the 2-t-butylanthraquinone (5.2 g, 19.5 mmol) (dissolved in 20 mL THF) was added dropwise to the reaction. Once the addition was complete the reaction was allowed to stir at room temperature overnight. The reaction was quenched with saturated aqueous ammonium chloride solution and ethyl acetate (100 mL) was added. The aqueous layer was removed and the organic layer was washed twice more with ammonium chloride solution. The organic layer was collected, dried ($MgSO_4$) and conc in vacuo to give a yellow oil which was used directly in the next step. The product was dissolved into 1,4-dioxane (100 mL) and a mixture of 1:1 $H_2O$:AcOH (50 mL) was added. Tin(II) chloride dihydrate (21.93 g, 97.45 mmol) was added and the reaction was heated at 50° C. for 3 hours. The reaction was cooled to room temperature and methanol (50 mL) was added. The reaction mixture was filtered and the precipitate washed with methanol. The solid was collected, dried and was purified by Kaufmann column (alumina, cyclohexane). Further purification was achieved by sublimation (twice) at 260° C. to give >99% purity of 2-tert-butyl-9,10-(2-methyl)-diphenylanthracene.

For the purposes of this specification and appended claims, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," include plural referents unless expressly and unequivocally limited to one referent. Thus, for example, reference to "a polar liquid" includes two or more different polar liquids. As used herein, the term "include" and its grammatical variants are intended to be non-limiting, such that recitation of items in a list is not to the exclusion of other like items that can be substituted or added to the listed items.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

What is claimed is:

1. A process for preparing 2-tert-butyl-9,10-bis-(β-naphthyl)anthracene comprising:
    reacting 2-bromonaphthalene with a metal while a reaction temperature is increased from −78° C. to room temperature to yield a naphthyllithium compound;
    cooling the reaction to −78° C. and adding 2-tert-butylanthraquinone to the reaction;
    reacting the naphthyllithium compound with the 2-tert-butylanthraquinone while the reaction temperature is increased from −78° C. to room temperature to yield a diol;
    reacting the diol with a reducing agent in a dioxane at 50° C. to yield the 2-tert-butyl-9-10-bis-(β-naphthyl)anthracene; and
    drying and purifying the 2-tert-butyl-9-10-bis-(β-naphthyl)anthracene by Kaufman column and sublimation at 320° C.,
    wherein the reducing agent is vanadous chloride in an acid and with water.

2. The process of claim 1, wherein the reaction is stirred at the room temperature when the naphthyllithium compound is reacted with the 2-tert-butylanthraquinone.

3. The process of claim 1, wherein the diol is represented by formula (3):

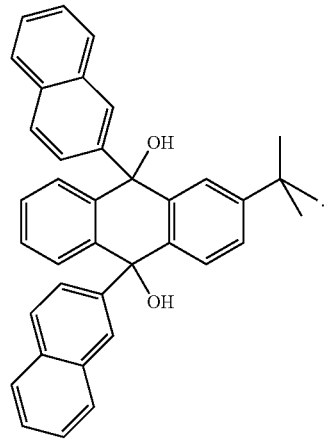

(3)

4. A process of preparing 2-tert-butyl-9-10-bis-(β-naphthyl)anthracene comprising:
    reacting 2-bromonaphthalene with a metal while a reaction temperature is increased from −78° C. to room temperature to yield a naphthyllithium compound;
    cooling the reaction to −78° C. and adding 2-tert-butylanthraquinone to the reaction;
    reacting the naphthyllithium compound with the 2-tert-butylanthraquinone while the reaction temperature is increased from −78° C. to room temperature to yield a diol; and
    reacting the diol with a reducing agent in a dioxane at 50° C. to yield the 2-tert-butyl-9-10-bis-(β-naphthyl)anthracene,
    wherein the reducing agent is titanous chloride in an acid with water.

5. The process of claim 4, wherein the diol is represented by formula (3):

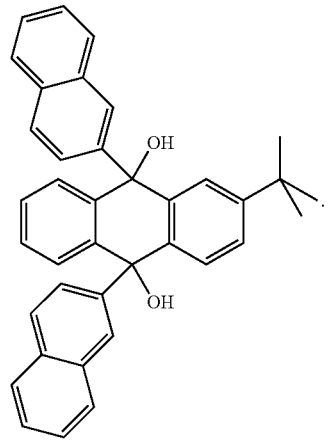

(3)

* * * * *